United States Patent
Cichocki, Jr.

(10) Patent No.: US 7,875,055 B2
(45) Date of Patent: Jan. 25, 2011

(54) ACTIVE SUTURE FOR THE DELIVERY OF THERAPEUTIC FLUIDS

(75) Inventor: Frank R. Cichocki, Jr., Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 71 days.

(21) Appl. No.: 10/909,717

(22) Filed: Aug. 2, 2004

(65) Prior Publication Data
US 2005/0125035 A1 Jun. 9, 2005

Related U.S. Application Data

(63) Continuation-in-part of application No. 10/727,367, filed on Dec. 4, 2003.

(51) Int. Cl.
*A61B 17/04* (2006.01)
(52) U.S. Cl. ........................... 606/228; 604/527
(58) Field of Classification Search ......... 606/222–232, 606/139; 604/93.01, 164.08, 164.09, 523, 604/524, 525, 526, 527
See application file for complete search history.

(56) References Cited

U.S. PATENT DOCUMENTS

| | | | | |
|---|---|---|---|---|
| 3,212,502 A | * | 10/1965 | Myers | 606/224 |
| 3,474,703 A | * | 10/1969 | Davis et al. | 87/1 |
| 3,918,455 A | * | 11/1975 | Coplan | 606/225 |
| 4,159,720 A | * | 7/1979 | Burton | 424/423 |
| 4,232,673 A | * | 11/1980 | Bucalo | 600/582 |
| 4,673,565 A | | 6/1987 | Di Luccio et al. | |
| 4,712,553 A | | 12/1987 | MacGregor | |
| 4,880,002 A | * | 11/1989 | MacGregor | 606/226 |
| 5,458,582 A | | 10/1995 | Nakao | |
| 5,538,735 A | | 7/1996 | Ahn | |
| 5,735,829 A | | 4/1998 | Cherian | |
| 5,797,886 A | | 8/1998 | Roth et al. | |

(Continued)

FOREIGN PATENT DOCUMENTS

FR 2747908 * 4/1996

(Continued)

OTHER PUBLICATIONS

International Search Report dated Jun. 10, 2005 for corresponding Appln. No. PCT/US2004/040488.

Primary Examiner—Gary Jackson
Assistant Examiner—Tuan V Nguyen
(74) Attorney, Agent, or Firm—Roberts Mlotkowski Safran & Cole, P.C.

(57) ABSTRACT

An active suture that can be used for the delivery of therapeutic fluids to the tissue surrounding a wound is disclosed. The active suture may include a connector designed to join a fluid source, such as a syringe, conventional IV delivery system, or infusion pump to an internal passageway that is embedded within a braided suture. The internal passageway may be comprised of a fine polymeric tube and is capable of conducting and emitting a fluid into at least a portion of the braided suture and surrounding tissue. The invention enables delivery of an efficacious volume of drug bearing solution on the order of milliliters per day, provides a high level of fluid delivery rate control enabling the physician to start or stop drug administration at his/her discretion, and offers a means of providing more than one type of medication that may be selected post-surgically in accord with unexpected patient symptoms that may arise.

4 Claims, 12 Drawing Sheets

U.S. PATENT DOCUMENTS

| | | | |
|---|---|---|---|
| 5,836,962 A * | 11/1998 | Gianotti | 623/1.51 |
| 5,891,101 A | 4/1999 | Wilcox et al. | |
| 5,914,973 A * | 6/1999 | Jiang et al. | 372/36 |
| 5,919,473 A | 7/1999 | Elkhoury | |
| 5,984,933 A | 11/1999 | Yoon | |
| 6,152,141 A | 11/2000 | Stevens et al. | |
| 6,264,600 B1 | 7/2001 | Grimm | |
| 6,368,315 B1 | 4/2002 | Gillis et al. | |
| 6,565,534 B1 | 5/2003 | Winters | |
| 6,626,885 B2 | 9/2003 | Massengale | |
| 2002/0029066 A1 | 3/2002 | Foerster | |
| 2002/0095133 A1 | 7/2002 | Gillis et al. | |
| 2003/0028204 A1 | 2/2003 | Li et al. | |
| 2005/0125034 A1 | 6/2005 | Cichocki | |
| 2006/0030883 A1 | 2/2006 | Cichocki, Jr. | |

FOREIGN PATENT DOCUMENTS

| | | |
|---|---|---|
| FR | 2747908 A | 10/1997 |
| GB | 1528955 A | 10/1978 |
| WO | WO 01/05210 A2 | 1/2001 |
| WO | WO 01/05210 A3 | 1/2001 |
| WO | WO 03/017854 A1 | 3/2003 |

* cited by examiner

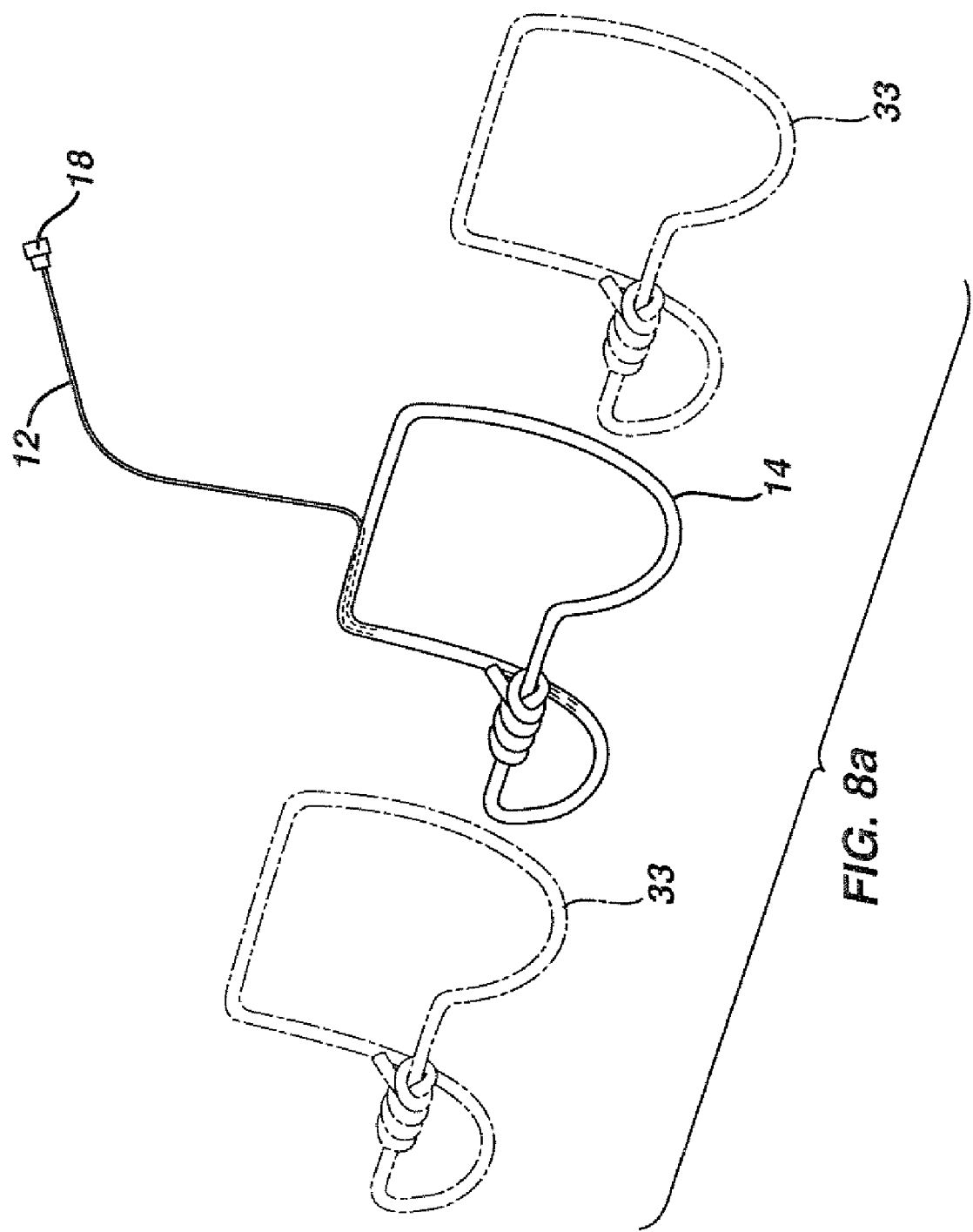

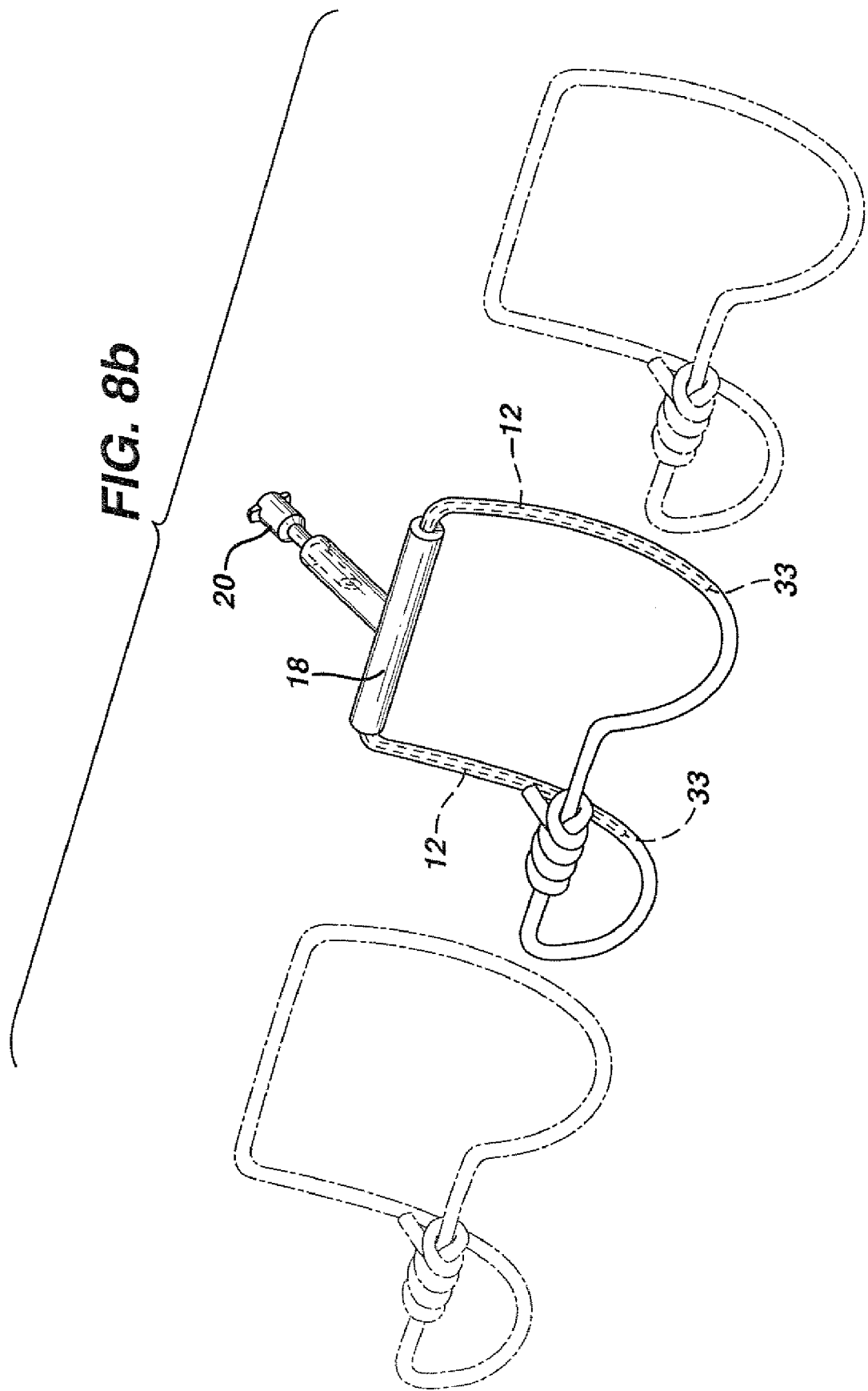

ACTIVE SUTURE FOR THE DELIVERY OF THERAPEUTIC FLUIDS

CROSS-REFERENCE TO RELATED APPLICATION

This application is a continuation-in-part of U.S. application Ser. No. 10/727,367 filed Dec. 4, 2003.

FIELD OF INVENTION

The present invention relates to devices that may be used to deliver therapeutic fluids to surgical wounds. More particularly the invention relates to functional sutures that may be used to emit therapeutic or bioactive fluids to the tissue surrounding the suture. In particular, the invention relates to a braided suture having an internal passageway capable of conducting a fluid along at least a portion of the length of the suture that may be attached on one end, through a connector, to a fluid source.

BACKGROUND OF THE INVENTION

Much benefit could be realized by delivering therapeutic fluids to the direct vicinity of the surgical wound. Reduced pain, enhanced wound healing, and reduced occurrence of surgical site infections are but a few potential benefits. However, the form and function of a device that could cost-effectively facilitate localized delivery of therapeutic fluids directly to the wound site over an extended period of time are not apparent. Intravenous (IV) delivery of medication to the patient following a surgical procedure is common practice. The physician may use an IV to deliver a wide variety of medications directly to the patient's blood stream over an extended period of time. Intravenous (IV) administration of medication is indeed a systemic method of drug delivery where the medication will circulate through the entire body before a portion of the medication is delivered to the wound site. Since much of the medication may be metabolized at other locations within the body before reaching the wound site, it is often necessary to increase the overall amount or concentration of medication to be delivered systemically with an IV in order for an efficacious amount to reach the wound site. However, in many cases, the increased concentration of medication that may provide the most efficacious result at the wound site, may not be safely delivered through an IV since toxic side effects may occur at various organs within the body. Other medications, such as certain local anesthetics, only provide an efficacious result when delivered locally and are simply not compatible with IV delivery methods.

Multiple injections in and around the surgical wound, before, during and after surgical procedures have been used in an effort to deter side effects and complications associated with surgical procedures. Although the syringe and hypodermic needle provide a means for localized drug delivery, the continuous delivery of medication via injection over an extended time period is not practical. Indeed, over time the medication dissipates to a concentration below that required to achieve a therapeutic effect and additional injections must be prescribed. Moreover, in the case where the surgical wound is the local target for drug treatment, multiple injections around the wound site may be required to achieve the desired therapeutic effect. The patient may suffer discomfort and repetitive disturbance if multiple injections must be repeatedly administered. As a further draw back, with this approach, the health care professional must dedicate their valuable time and attention to repeatedly apply localized injections.

In order to address the aforementioned shortcomings of the IV and injections for the localized and continuous delivery of therapeutic fluids, a number of specialized infusion catheters for use in the wound site have been developed. These specialized infusion catheters typically exhibit multiple perforations along their lengths and are connected to a reservoir and pump that contain and feed the therapeutic liquid to the infusion catheter, for example as described in U.S. Pat. Nos. 5,458,582, 5,891,101 and 6,626,885. The infusion catheter itself may be placed directly into the surgical incision and held in place by closing the wound around it. However, a greater risk of infection and compromised wound healing may be associated with this deployment method since the infusion catheter may serve as a pathway for pathogens to enter the surgical incision. More commonly, the infusion catheter is passed through the skin and subcutaneous tissue in the vicinity of the wound, leaving the tip of the catheter within the surgical incision and the body of the catheter in healthy tissue surrounding the wound. It is important to note that the implantation of an infusion catheter in this manner commonly requires the use of a cannula to puncture and guide the infusion catheter though the skin and subcutaneous tissue and into the surgical incision site. Although these catheters provide a means of continuously delivering a therapeutic fluid to the wound, a number of drawbacks exists. Many devices such as described in U.S. Pat. No. 6,626,885 require the use of cannulas and additional puncture wounds in the vicinity of the surgical wound to firmly secure the catheter in place, while others described in U.S. Pat. Nos. 5,891,101 and 5,458,582 require the use of additional sutures or a modification of the suturing procedure. Even so, the infusion catheter may not be firmly anchored and accidental removal of the catheter from the wound site by the patient is not uncommon. Alternatively, in order to reduce patient discomfort and other complications associated with catheter removal, some catheter devices such as described in U.S. Pat. No. 5,458,582 may be produced from bioabsorbable materials. However, the implantation of bioabsorbable catheters increases the amount of material that must be absorbed and metabolized by the body, and it is generally desirable to keep this bioburden to a minimum. Finally, there are significant additional costs, ranging from hundreds to thousands of dollars, associated with the use of these specialized catheters and the supporting reservoirs and pumps that must be employed for their operation.

A suture that could be used for localized and continuous drug delivery could satisfy the unmet needs of the aforementioned devices. The suture is implanted into the tissue surrounding the wound, which is indeed the region that may benefit most from localized drug delivery. Further, since the suture must be present in most cases to achieve wound closure, the number of invasive procedures that a patient must suffer is not necessarily increased. Moreover, suture needles attached to one end of the suture may be used to penetrate tissue surrounding the wound and facilitate placement of the fluid infusing suture. The suture may be secured in the wound by making a knot in one end to prevent accidental removal. Moreover the flexibility exhibited by a suture is considerable greater than the flexibility exhibited by infusion catheters, consequently, the suture may be placed in a complicated pattern or in locations that would be hard to reach with a conventional infusion catheter. Although a number of benefits may be achieved if drug delivery from a suture were possible, the form and function of such a device is not apparent.

The concept of hollow monofilament sutures was first disclosed in U.S. Pat. No. 3,918,455. Although this patent focused on the use of hollow sutures to facilitate attachment to the suture needle, it was also suggested that the bore of the hollow suture could be filled with a fluid at the time of its installation to expedite dissolution of the suture material or render the suture visible by X-radiography. It was further suggested that the tube could be so extruded and drawn to be converted into a microporous state. In this state, the polymer comprising the wall of the hollow suture would permit fluid contained in the bore of the suture to gradually diffuse through the wall into the surrounding tissue. In U.S. Pat. No. 5,984,933 an apparatus for suturing tissue has been described. Although the patent focuses on a method and device to facilitate endoscopic suturing, it was suggested that the suture material of the device could be solid or hollow, and when the suture material is hollow, small holes in the wall of the suture can be formed to enable medicaments contained in the bore of the suture to leach out into the surrounding tissue. Although these patents suggest that hollow sutures may be used to contain, and in some embodiments even slowly emit a therapeutic fluid, there are some critical shortcomings that remain unaddressed. First of all, monofilament sutures are flaw sensitive. The introduction of pores or perforations into the wall of the hollow suture may result in a substantial decrease in the strength performance of the suture and lead to its inability to insure secure closure of the wound. Secondly, the amount of medicine that may be contained inside of a hollow suture is small. Indeed the maximum amount of drug bearing solution that may be contained within most hollow sutures is on the order of 0.005 ml or less, whereas many commercially available drug bearing solutions are efficacious only in quantities in excess of 1 ml. For example, anesthetic agents such as marcaine, lidocaine, bupivacaine, mepivacaine and procaine are typically injected into the tissue surrounding an incision or wound in a buffer solution at an overall volume ranging from 5 to 30 ml, which is 500 to 3000 times greater than the dose that is applicable with the hollow sutures disclosed in U.S. Pat. Nos. 3,918,455 and 5,984,933. Finally, once the hollow suture is implanted into the tissue surrounding the wound, the drug delivery rate is dictated by the rate at which the fluid leaches or diffuses through the multiple perforations or pores. Active control of the drug delivery rate and continuous drug delivery are not possible. Furthermore, if an adverse reaction to the drug occurs, the suture must be excised from the wound to terminate drug delivery.

U.S. Pat. No. 4,159,720 describes a means for infusing liquids into tissue. The preferred embodiment comprises a reservoir for containing fluids attached outside the body that feeds liquid to an absorbent wick. The absorbent wick may be made from materials commonly used in the manufacture of sutures and may be installed in the tissue in a variety of ways including placement inside of the incision or deployment in the tissue surrounding the wound. The invention relies on capillary action to draw fluid in and control the delivery rate. As such, fluid delivery rate may not be increased or decreased at the physician's discretion. Moreover, the rate of fluid influx will depend on the type of wicking material used and the thickness and length of the wick installed. It is also important to note that in the cases when the suture is comprised of a material or is coated with a material that is not wetted by the fluid, wicking action will not occur and the device will not function. Even when the fluid to be delivered does indeed wet the wick, one may expect the fluid delivery rate driven by capillary forces that may be evolved within a suture to be several orders or magnitude slower than fluid delivery rates achievable by other means such as IV, infusion catheter, or injection.

It may be desirable to have of a suture that serves the multiple functions of wound closure and drug delivery. However, unlike the aforementioned examples of prior art, the suture should: 1) not compromise critical performance characteristics such as strength of the suture, 2) enable delivery of an efficacious volume of drug bearing solution on the order of milliliters not microliters, 3) provide a high level of drug delivery rate control and enable the physician to start or stop drug administration at his/her discretion, 4) provide a means of providing more than one type of medication that may be selected post-surgically in accord with unexpected patient symptoms that may arise, 5) function regardless of the composition and wetting characteristics of the suture material.

A suture that satisfies the aforementioned criteria for wound closure and drug delivery is disclosed herein. It is important to note that while the device disclosed herein may be used in a multifunctional manner to close wounds and infuse fluids to a wound site, simpler applications where the suture acts solely as an infusing device are likewise possible and useful. Components of the suture may include a connector designed to join a fluid reservoir, such as an IV, or syringe, or infusion pump to a braided suture that contains at least one internal passageway capable of conducting a fluid along at least a portion of its length. The therapeutic fluid passes from the reservoir, through the connector, into the internal passageway and into the interstices between the multiple filaments of the braided suture. The integrity of the braided suture is not compromised in the design of this device and critical performance characteristic such as suture strength are maintained above United States Pharmacopia, USP, standards. By employing a connector to link the fluid conducting element of the suture to an external reservoir, the amount of therapeutic fluid that may be delivered through the suture may be increased to a volume that is efficacious. Moreover, by regulating the supply of therapeutic fluid, the drug delivery rate may be actively controlled and more than one type of medication may be supplied as needed.

SUMMARY OF INVENTION

Described herein is an active suture comprising a braided suture having proximal and distal ends and an outer diameter; and at least one passageway coaxial with at least a portion of the braided suture, and having proximal and distal ends and a diameter that is less than the outer diameter of the braided suture; wherein the distal end of the at least one passageway is disposed between the proximal and distal ends of the braided suture.

Also described is an active suture comprising a braided suture having an outer diameter; and a tube coaxial with at least a portion of the braided suture, having an outer diameter that is less than the outer diameter of the braided suture and an inner diameter, and having one or more opening therein; wherein the ratio of the outer diameter of the tube to the inner diameter of the tube is greater than 1.7.

Further described is an active suture comprising a first braided suture having an outer diameter and having embedded therein a coated fiber tow or coated braided suture coaxial with at least a portion of the first braided suture, said coated fiber tow or coated braided suture having an outer diameter that is less than the outer diameter of the first braided suture, and said coated fiber tow or coated braided suture having one or more opening therein.

A method of administering a fluid to a wound is also described, where the wound has been closed using a braided suture having proximal and distal ends, an outer diameter, at least one passageway coaxial with at least a portion of the braided suture, said passageway having proximal and distal ends, an opening at the distal end and a diameter that is less than the outer diameter of the braided suture, wherein the distal end of the at least one passageway is disposed between the proximal and distal ends of the braided suture; and a connector attached to the proximal end of the at least one passageway; such that the distal end of the at least one passageway is at or in the proximity of the wound.

Further described herein is a method of closing a wound, optionally in combination with administering a fluid to a wound, using a suture/needle assembly comprising a braided suture having proximal and distal ends, an outer diameter, at least one passageway coaxial with at least a portion of the braided suture, said passageway having proximal and distal ends, an opening at the distal end and an outer diameter that is less than the outer diameter of the braided suture, wherein the distal end of the at least one passageway is disposed between the proximal and distal ends of the braided suture; a surgical needle attached to the distal end of the braided suture; and a connector attached to the proximal end of the at least one passageway.

BRIEF DESCRIPTION OF FIGURES

FIGS. 8a and 8b are schematic depictions of double-armed active sutures deployed in an interrupted mattress stitch pattern.

DETAILED DESCRIPTION OF INVENTION

The invention disclosed herein is an active suture that may be used to deliver one or more therapeutic liquids to the direct vicinity of the wound, in a continuous or discontinuous fashion, over an extended period of time, without the need for additional invasive devices or procedures, without substantially increasing the amount of material that must be metabolized by the body, and without the need for investment in auxiliary devices or equipment. Deployment of the active suture in tissue may be conducted without the need for cannulas and guide wires commonly used with conventional infusion catheters.

Figure 1A:
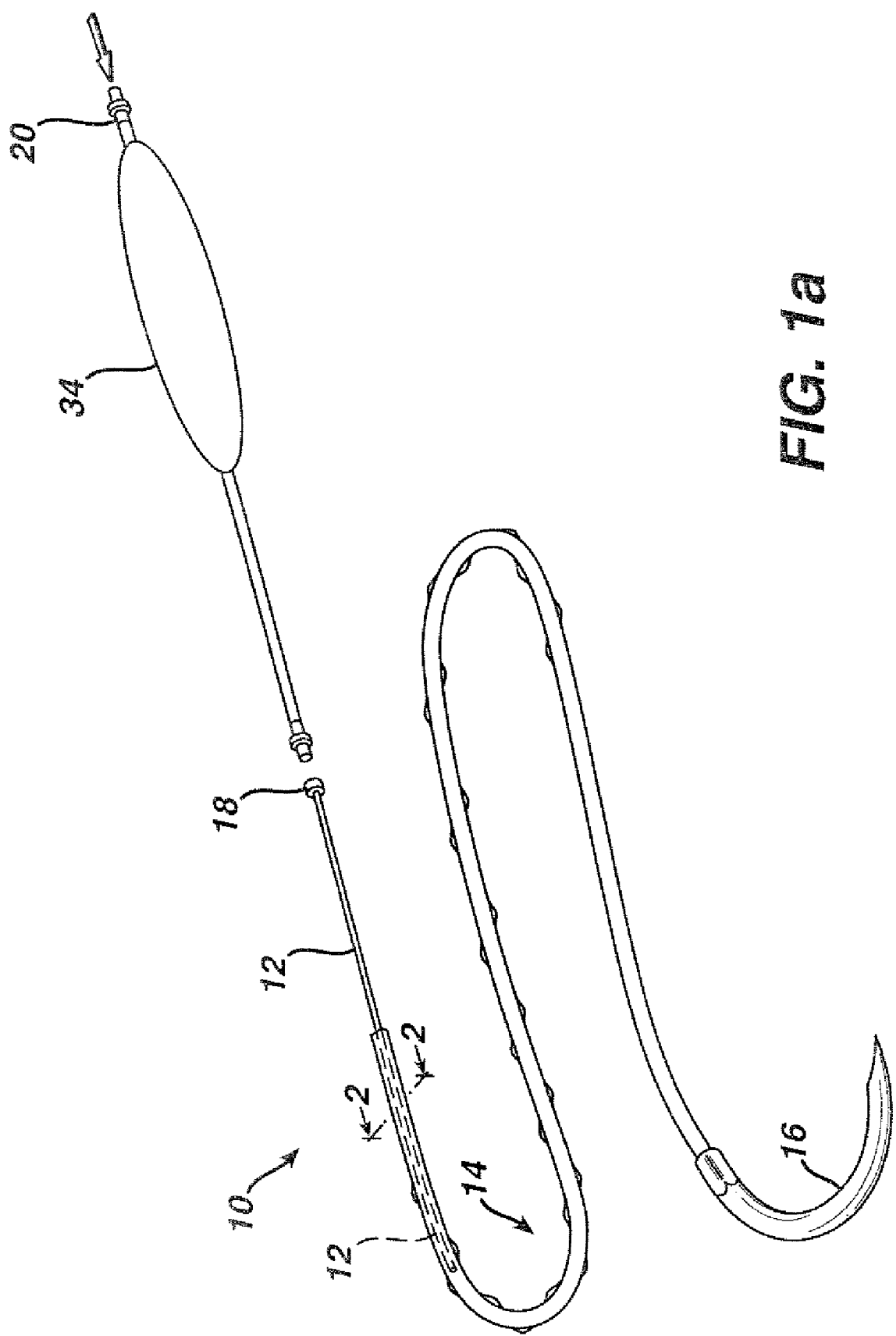
FIGS. 1a and 1b are schematic representations of an active suture.

The active suture 10, schematically depicted in FIG. 1a, comprises a braided suture 14 with one or more internal passageway 12 capable of conducting and expelling a therapeutic fluid into at least a portion of the braided suture. The active suture may be connected to a suture needle 16 at the distal end. The internal passageway that is located in at least a portion of the suture may extend from the suture and a connector 18 may be fitted to the proximal end of the said passageway to enable fluid communication between an external fluid reservoir and the internal passageway 12 contained within the active suture. The connector 18 may be designed to directly accommodate a variety of conventional fluid reservoirs, including but not limited to a syringe, or conventional medical tubing attached to intravenous (IV) delivery systems or a variety of fluid infusion pumps, such as described in U.S. Pat. Nos. 6,626,392, 6,626,855, 5,284,481 and 5,080,652. As described in U.S. Pat. Nos. 6,626,392 and 6,626,855 an inflatable reservoir 34 produced from an elastomeric polymer may be attached in series between the connector 18 and the syringe fitting 20. A syringe may be attached to the syringe fitting 20 and used to inflate the reservoir. A variety of commercially available fittings including but not limited to: luer locks, one-way valves, two-way valves, and T-fittings may be used. Specially made fittings that limit connection of the active suture to a specific reservoir, syringe, or fluid source may be used in lieu of commercially available fittings. Other accessory components as described in U.S. Pat. No. 6,626,855 that filter fluids or limit or block flow may be integral to the fluid source. Additional devices that measure flow rate, for example as described in U.S. Pat. No. 6,371,937, may be incorporated into the tubing used to connect the infusion pump to the active suture. Fluid may be delivered from an external fluid source, through the connector and internal passageway and out the interstices of the braided suture to tissue surrounding the suture before, during, or after the wound closure procedure. The pressures exerted on or by the external fluid source may exceed any pressures that can evolve within the braided suture due to capillary or diffusional phenomena. Further, by controlling the pressures exerted on or by the external fluid source, the supply of fluid may be regulated and the fluid delivery rate may be actively controlled.

Figure 1B:
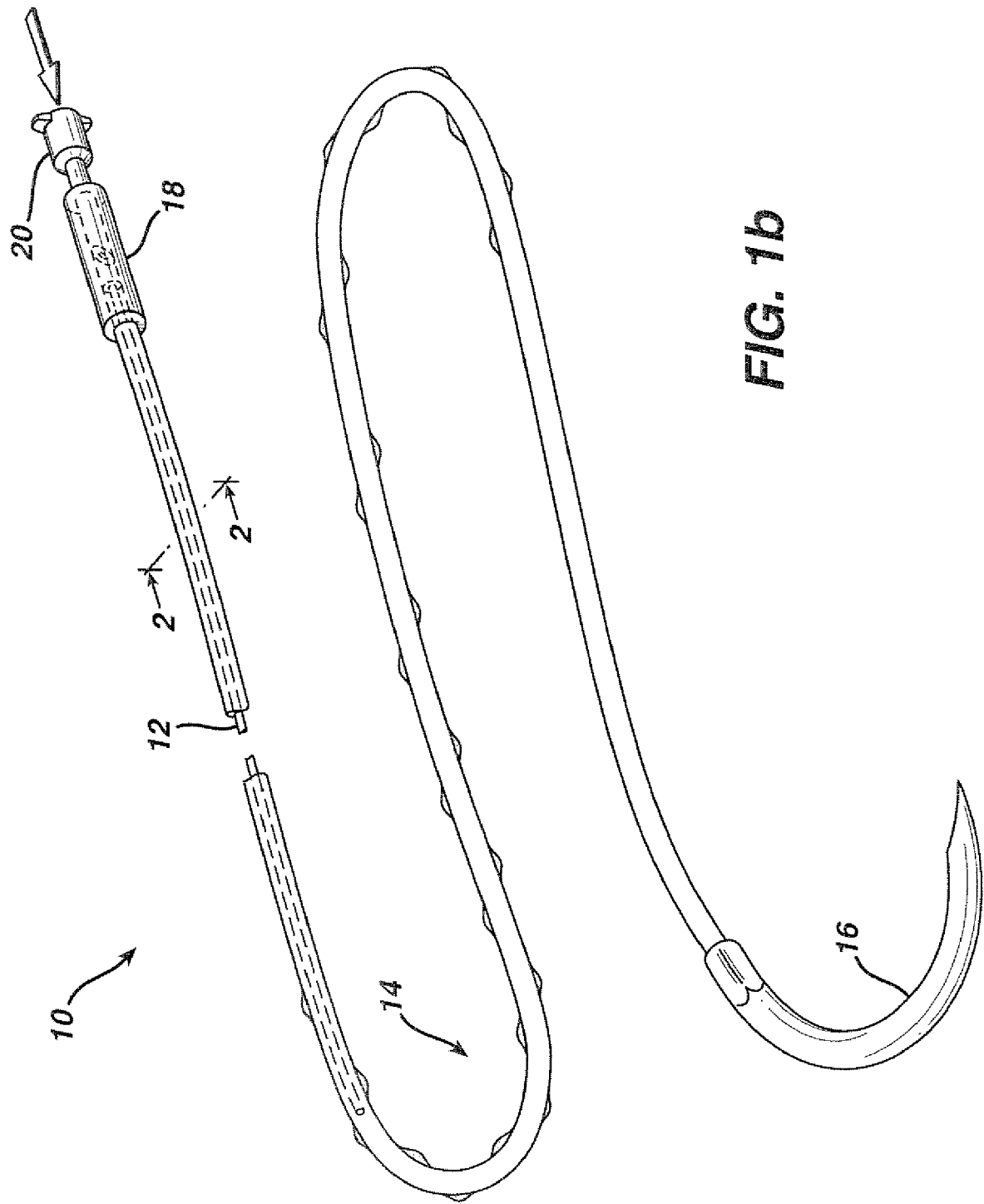

Alternatively, as depicted in FIG. 1b, the active suture 10 may be connected to a suture needle 16 at the distal end and a connector 18 may be fitted to the proximal end of the internal passageway 12 to enable fluid communication between an external fluid reservoir and the internal passageway 12 of the active suture. The connector 18 may be designed to directly accommodate a variety of conventional fluid reservoirs, including but not limited to syringes, fluid pumps or intravenous (IV) delivery systems. As shown in FIG. 1b, the connector may fit around both the internal passageway and braided suture of the device.

Figure 2A:
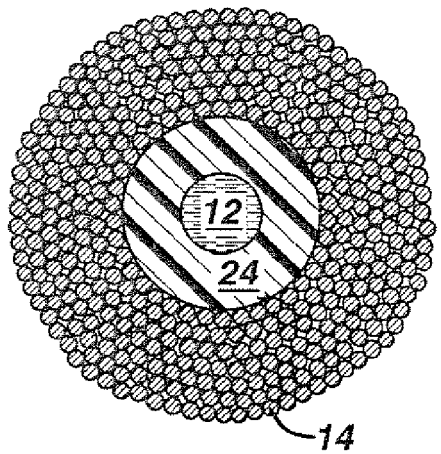
FIG. 2a is a schematic cross-sectional view along section 2-2 of FIGS. 1a or 1b displaying a fine tube at the core.
Figure 2B:
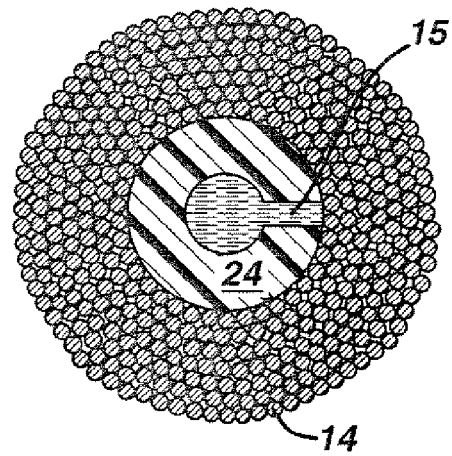
FIG. 2b is a schematic cross-sectional view along section 2-2 of FIGS. 1a or 1b displaying a fine tube at the core with a slit continuous along the length of the fine tube.
Figure 3A:
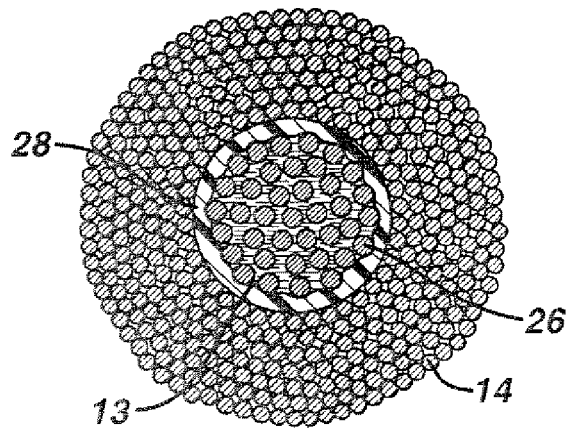
FIG. 3a is a schematic cross-sectional view along section 2-2 of FIGS. 1a or 1b displaying a coated fiber tow at the core.
Figure 3B:
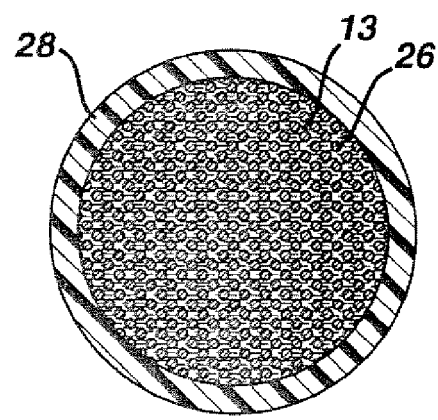
FIG. 3b is a schematic cross-sectional view displaying a coated fiber tow.

A critical component of the active suture is the internal passageway for conducting fluid to the interstices of the braided suture. Transverse cross-sectional views of a braided suture taken along 2-2 of FIG. 1a or 1b that contain an internal passageway are schematically depicted in FIGS. 2a, 2b, 3a and 3b. As shown in FIG. 2a, the lumen 12 of a polymeric tube 24 that is incorporated into a braided suture 14 may serve as the internal passageway. As shown in FIG. 2b, the tube 24 may contain a slit or fine opening 15 along its entire length to serve as a channel for fluid egress into the braided suture 14. Tubes used as the internal passageways that are incorporated into the braided sutures may take a variety of cross-sectional shapes including but not limited to circular, rectangular, and triangular. Likewise, the fluid conducting lumen may assume a variety of shapes including circular, triangular, rectangular, as well as cross or star-shaped. Alternatively, as shown in FIGS. 3a and 3b, the interstices 13 between the filaments of a fiber tow 26 or braided suture that has been coated with a continuous polymer sheath 28, or otherwise surrounded by a polymeric tube and embedded coaxially in braided suture 14, may serve as the internal passageway. As in FIG. 3b, the polymer coated filaments of a fiber tow, or the polymer coated braided suture may serve as a stand alone fluid conducting suture as well.

Figure 4A:
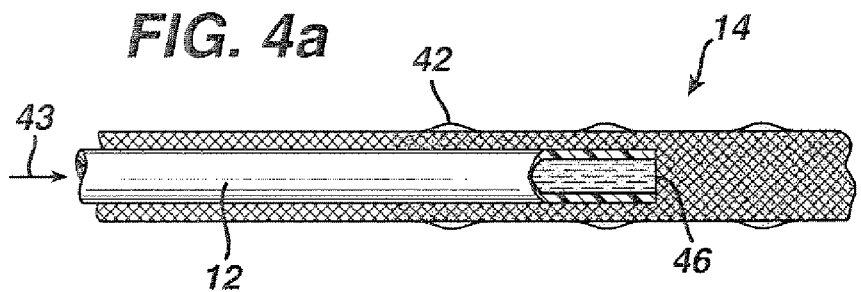
FIGS. 4a, 4b, 4c, 4d, and 4e are cut away sections of the fluid emitting segments of the various embodiments of active sutures.

As depicted in the longitudinal cross-sectional view of a portion of an active suture shown in FIG. 4a, the internal passageway 12 may terminate within the braided suture 14 at a location between the connector and the suture needle. In this embodiment, fluid would enter through the connector 18 in FIG. 1, and travel within the proximal end of the active suture reaching location 43 of FIG. 4a, continuing on through the internal passageway 12, out the open end of the passageway 46, and into the interstices of the braided suture 14. The fluid accumulates within the interstices of the braided suture 14, eventually reaching the surface 42 where it may be dispensed into the surrounding tissue. In an alternate embodiment, the fluid may be emitted from several locations along the length of the internal passageway. As depicted in the longitudinal cross-sectional view shown in FIG. 4b, the internal passageway 12, receiving the fluid from location 43, may emit the fluid into the braided suture though one or more openings 48 along the length of the passageway as well as through the truncated end of the passageway 46. Openings in the passageway may be of practically any geometrical shape including, but not limited to circular, oval, and rectangular. Openings may also be of different sizes or be packed more densely at one location than another to achieve different rates of fluid delivery from different locations along the suture. In another embodiment, the internal passageway, containing at least one opening 48, may pass along the entire length of the active suture from the proximal end of the suture to the suture needle. As depicted in the longitudinal cross-sectional view of a segment of an active suture shown in FIG. 4c, fluid entering at location 43 may be emitted from one or more openings 48 along the length of the active suture. As with the embodiment depicted in FIG. 4b, the openings may assume a variety of geometrical shapes and may be distributed in variety of ways along the length of the suture. A continuous opening in the internal passageway, such as the channel 41 schematically depicted in FIG. 4d, may also be used to facilitate fluid egress from the internal passageway to the braided suture and wound site. The channel may be located in a straight line, for example along the length of a tube, or may be made to spiral along the length of a tube. In this embodiment fluid may egress from any location along the length of the active suture. Finally, a braided suture that is surrounded by a tube or polymeric coating along a portion of its length, as schematically depicted in a longitudinal cross-sectional view in FIG. 4e, may also be employed to transport a fluid from the connector 18 shown in FIGS. 1a and b to the braided suture. It is important to note that active sutures with a combination of fluid conducting elements may be produced. For example, a fluid conducting element that bridges the space between the connector 18 and the proximal end of the braided suture, as shown in FIG. 1a, may a fine tube. This fine tube may then fit into and be secured within a slightly larger tube embedded inside the braided suture that exhibits multiple perforations or channels along its length to form the internal passageway of the active suture.

Figure 5A:
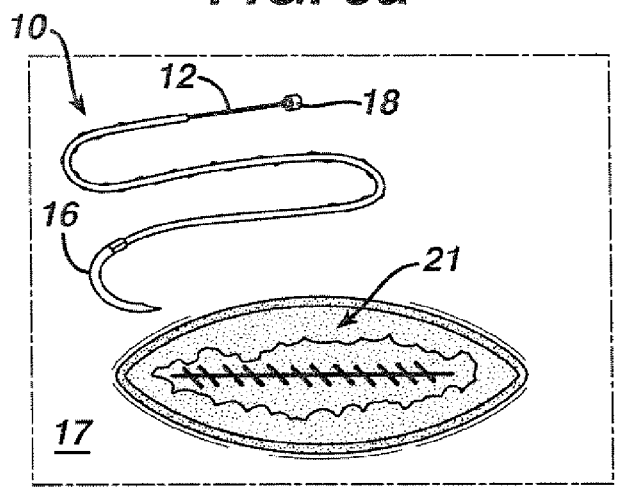
FIGS. 5a, 5b and 5c schematically represent the sequential steps used to deploy an active suture as a simple fluid infusion device.
Figure 5B:
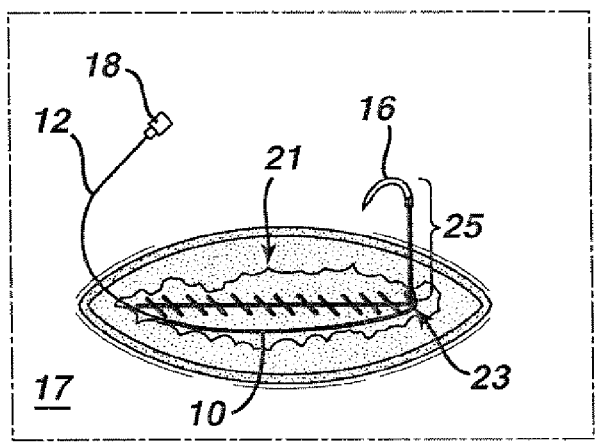
Figure 5C:
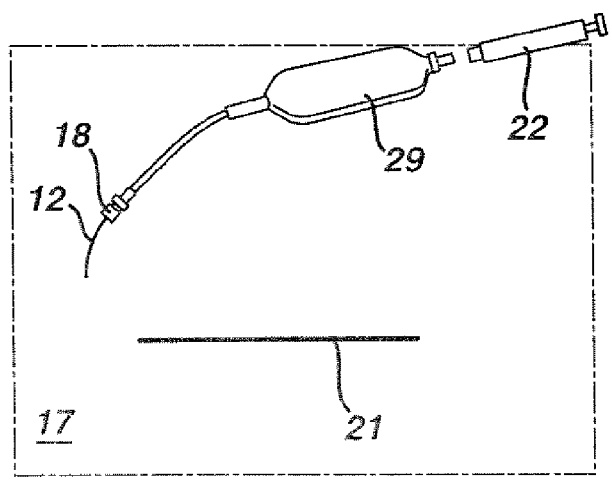

The active suture may be deployed to deliver therapeutic fluids in a variety of ways. With the simplest method, the active suture may be used to infuse a therapeutic fluid to the wound site without serving as a device for wound approximation or closure. FIGS. 5a, 5b and 5c schematically represent the sequential steps used to deploy an active suture 10 as a fluid infusion device. The suture needle 16 is passed through the skin 17 and subcutaneous tissue adjacent to the wound and continues on into the incision site 21 itself as shown in FIG. 5a. The active suture is then pulled through the hole produced by the suture needle 16 and positioned inside the incision, as shown in FIG. 5b. At this stage, a portion of the internal passageway 12 and connector 18 remain external to the body. A knot or series of knots 23 may be tied in the proximal end of the active suture to secure it in place and to prevent accidental removal of the device, as shown in FIG. 5b. The excess suture including the suture needle 25 are trimmed away and discarded. The incision 21 is then closed with conventional means using additional sutures, staples, or skin adhesives. In a final step shown in FIG. 5c, the therapeutic fluid is supplied to the active suture via a syringe 22 or reservoir pump 29.

Figure 6A:
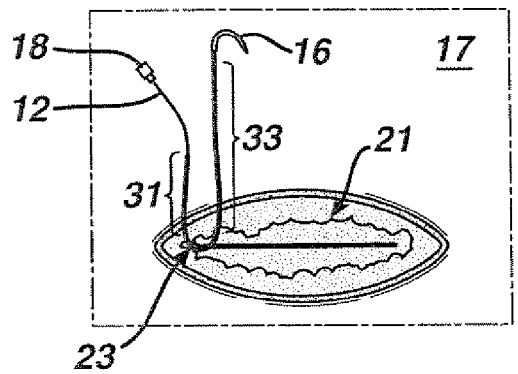
FIGS. 6a, 6b, 6c and 6d schematically represents the sequential steps used to deploy an active suture as both a suture for wound closure and fluid infusion.
Figure 6B:
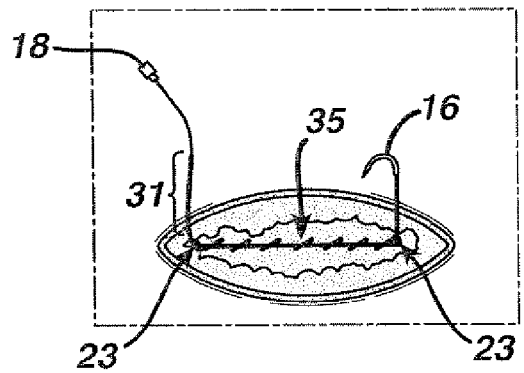
Figure 6C:
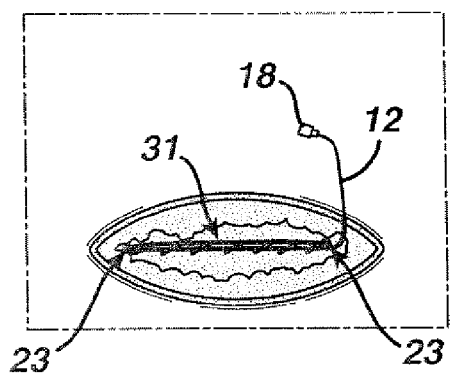
Figure 6D:
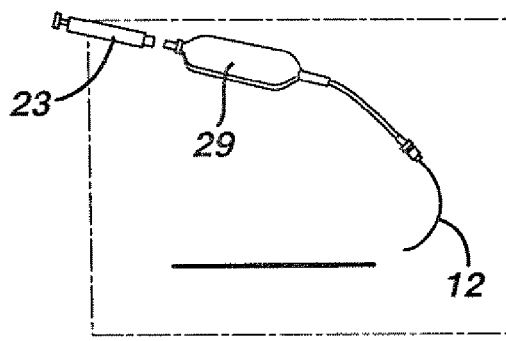

Alternatively, the active suture may be deployed to serve as both a suture for wound closure and a fluid infusion device. FIGS. 6a, 6b, 6c and 6d schematically represents the sequential steps used to deploy an active suture, of the type shown in FIG. 1a, as both a suture for wound closure and fluid infusion. In the first step, a series of knots 23 are tied across the incision at a location in the active suture between the distal end of the internal passageway 12 and the suture needle 16. This step in essence divides the suture into two segments, a segment to be used for wound approximation 33 and a segment to be used for fluid infusion 31. The segment of the suture that is located between the knots and suture needle 33 is then deployed in a continuous stitch 35 to approximate tissue, as shown in FIG. 6b. The infusion segment of the suture 31 in then placed over the line of stitches 35, as shown in FIG. 6c. Alternatively, the infusion segment 31 may be secured underneath one or more of the continuous stitches during the wound approximation step described in FIG. 6b. The incision is then closed by conventional means using additional sutures, staples, and/or skin adhesives. In a final step, FIG. 6d, the therapeutic fluid is supplied to the device via a syringe 23 or reservoir pump 29.

As an alternative to the deployment methods described above, instead of implanting the active suture at the site of the incision, the active suture may be implanted in the tissue surrounding the incision. Implantation may be conducted through the skin by using the suture needle 16 of FIG. 1a, and 1b, at any time before, during, or after the surgery. As a further alternative, the active suture may be implanted in any tissue that requires delivery of a therapeutic fluid regardless of the location or operative procedure, provided its presence does not cause undue trauma to the surrounding tissue.

It is important to note that in addition to the method of delivering the therapeutic fluid to the wound after closure of the wound, as previously described, delivery of the therapeutic agent may occur perioperatively during the deployment of the active suture. Indeed in certain instances it may be desirable to pre-load or wet-out the active suture with a therapeutic fluid even before deployment. A further variation may involve delivery of one type of therapeutic fluid pre-operatively or perioperatively, followed by delivery of another type of therapeutic fluid post-operatively.

Figure 7A:
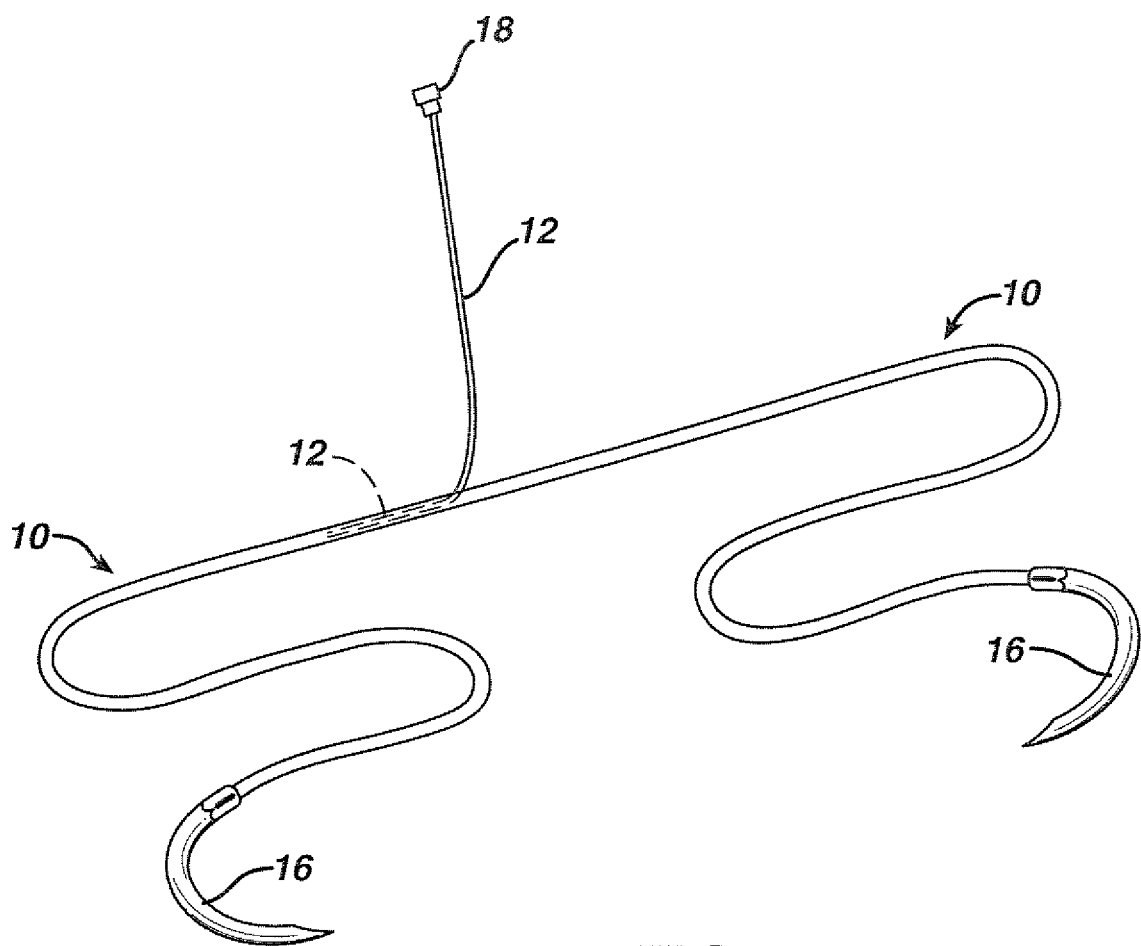
FIGS. 7a and 7b are schematic representations of the double-armed embodiment of the active suture.
Figure 7B:
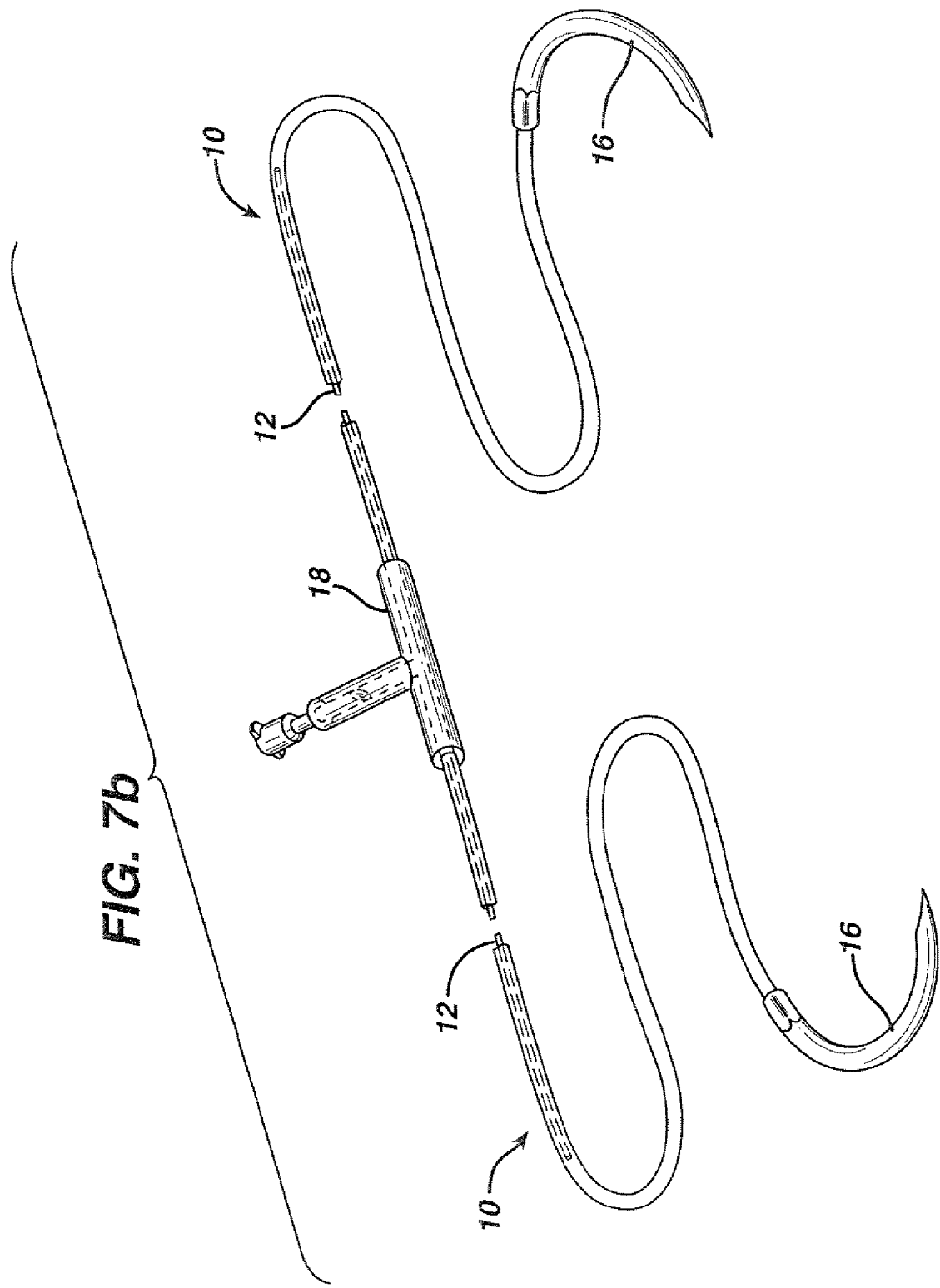

The invention may also be embodied in the form of a double-armed suture, as schematically depicted in FIGS. 7a and 7b, wherein two suture needles 16 and a single connector are employed. In these embodiments, a connector 18 designed to receive fluid from an external fluid reservoir is attached either to a tube that extends from the center portion of the active suture, FIG. 7a, or to the active suture 10 itself, FIG. 7b, in a manner that enables fluid communication with the internal passageways 12 of the active sutures. The double-armed suture may also be deployed in a variety of ways.

Schematic representation of double-armed sutures 10 used with an interrupted horizontal mattress stitch are shown in FIGS. 8*a* and 8*b*.

In the case where a reservoir pump or other continuous fluid supply means is connected to the active suture, the rate at which the fluid is emitted from the active suture is controlled predominantly be three factors: fluid viscosity, applied pressure, and passageway design. The Hagen-Poiseuille relationship for fluid flow through a cylindrical pipe may be used to approximate the volume flow rate of the fluid through the active suture with a passageway described by FIGS. 2*a* and 4*a*.

Volume Flow Rate=(π*Applied Pressure*Radius)/
(8*fluid viscosity*Passageway length)

where, Applied Pressure is the pressure exerted by the fluid source, Radius is the effective radius of the internal passageway through which the fluid passes, and the Passageway length is the effective length of the internal passageway from the connector to the location of the opening in the passageway. If an IV is used, the applied pressure may be determined by the height of the IV above the wound site where applied pressure=fluid density*gravitational
constant*height of the IV above the patient.

Figure 9:
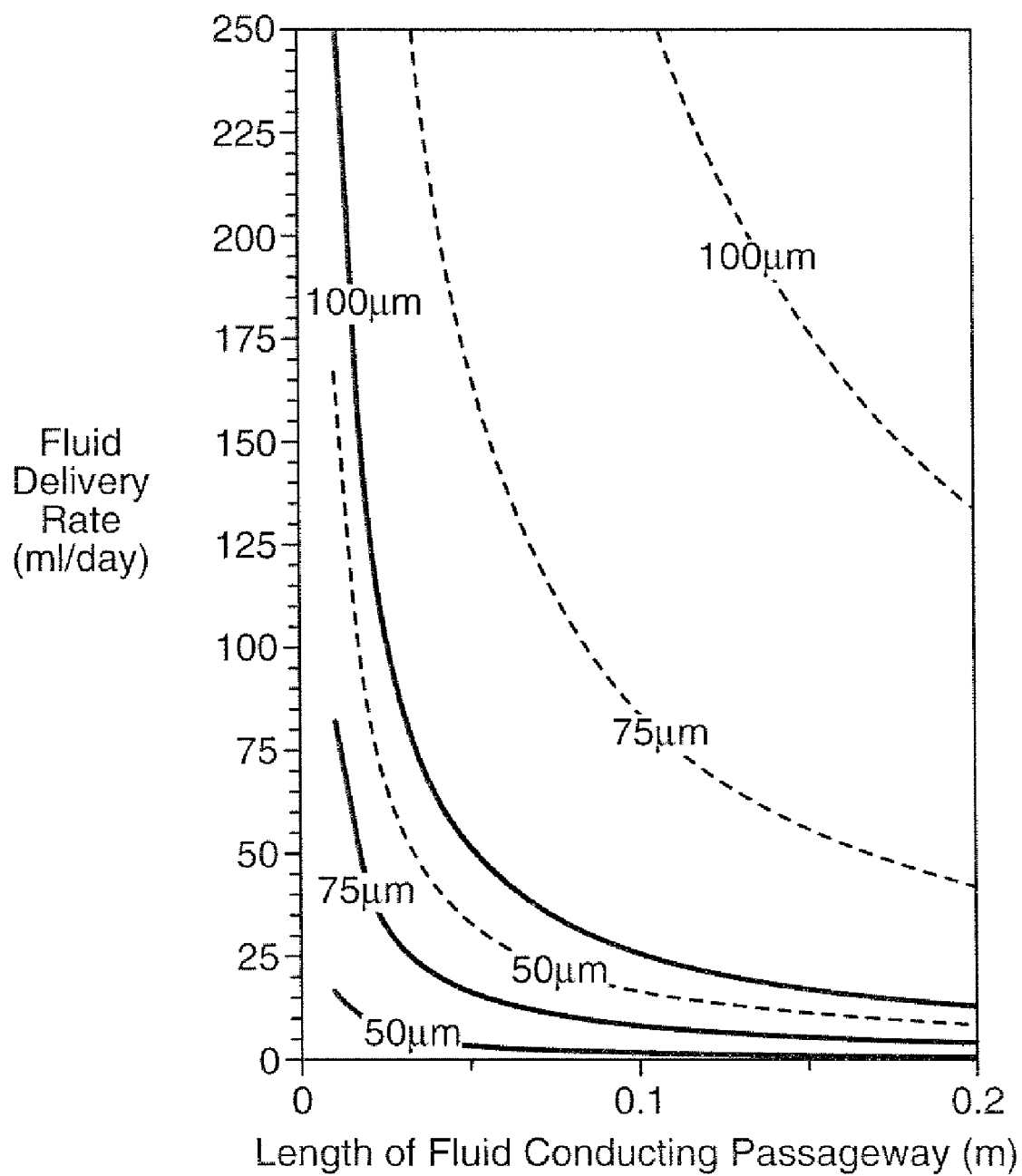
FIG. 9 is a graph of fluid delivery rate plotted against the length and diameter of the internal passageway at two different applied fluid pressures.

For example if the IV bag is held approximately one meter above the wound site, approximately 0.1 atmosphere (atm) of applied pressure would drive the fluid through the active suture. If an elastomeric inflatable reservoir, 34 in FIG. 1*a*, is used, the applied pressure that drives the fluid through the active suture may be as high as one atmosphere. Finally fluid pumps, commonly used in conjunction with IV delivery systems, are tunable and may be used to deliver the fluid to the active suture at a variety of pressures and rates. In FIG. 9, the Hagen-Poiseuille relationship has been used to estimate the volume flow rate of water at standard temperature and pressure (STP) through active sutures that contain tubular internal passageways, similar to the embodiment depicted in FIG. 1*a*, 2*a* and 4*a*, with lumens having inside diameters of 50, 75, and 100 μm that terminate within the braided suture at a distance of less than 0.2 m from the connector. The solid curves of FIG. 9 represent the range of delivery rates attainable with 0.1 atm of applied pressure. Elastomeric reservoir pumps typically supply pressures on the order of 0.1 to 1 atm of pressure. The dashed lines of FIG. 9 represent the range of delivery rates attainable with approximately 1 atm of applied pressure. Both lumen diameter and length of the internal passageway strongly influence the rate of fluid flow, with smaller diameter lumens and longer passageways resulting in reduced delivery rates. It is important to note that FIG. 9 provides an estimate of drug delivery rate in the absence of knots. Knotting of the suture produces a more tortuous path for the internal passageway and can lead to slower delivery rates.

In some applications, it will be desirable to tie knots in the active suture to facilitate wound closure. In many cases, a wound closure procedure, such as the procedure sequentially depicted in FIGS. 6*a*, 6*b*, 6*c* and 6*d*, may eliminate the need to tie knots in the portion of the active suture containing the internal passageway. In this way, the device may be used as both a suture for wound closure and a device for the infusion of therapeutic fluids without adversely impacting the control of fluid delivery rate. However, if a procedure is adopted which requires the use of a knot in the portion of the active suture containing the internal passageway, the internal passageway must remain intact in order for the active suture to conduct fluid past the location in which the knot is placed. If the interstices of the coated fiber tows or coated braided sutures are employed as the internal passageway of the active sutures, as schematically depicted in FIGS. 3*a* and 3*b*, the interstices therein will remain intact. However, if fine tubes are used in lieu of a coated fiber tow or coated braided suture to form the internal passageway, collapse and closure of the lumen can occur upon knot tying. In order to prevent closure of the lumens, tubes with sufficiently thick walls must be employed. Variables that influence the likelihood of collapse of the lumen inside of knots include thickness of the braided suture in which the internal passageway is imbedded, the stiffness of the tube, strength of the tube, and the overall tension applied in forming the knots. For active sutures that will be tied into surgically acceptable knots such as square knots or surgeons knots, preferably the ratio of the tube outside diameter (O.D.) to inside diameter (I.D.) is greater than 1.7 and more preferably, the ratio of the O.D. to I.D. is greater than 2.0 for most polymeric materials that are currently employed in sutures.

Figure 4B:
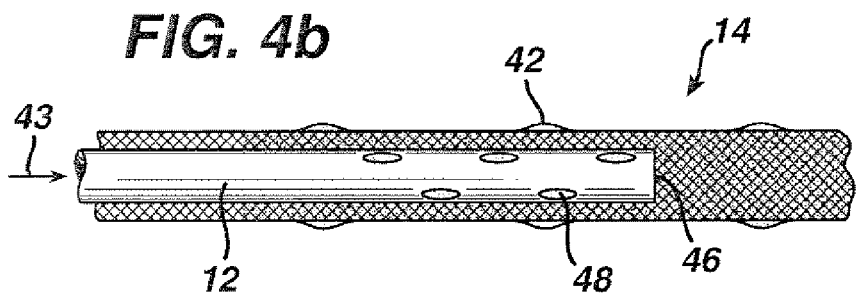
Figure 4C:
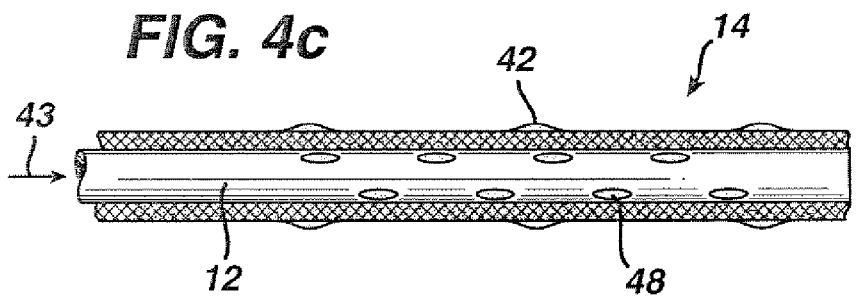
Figure 4D:
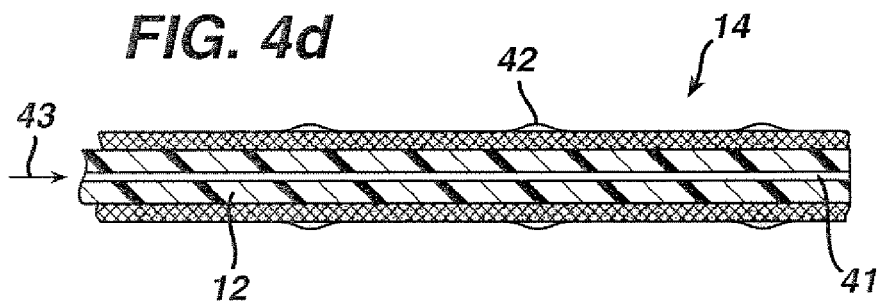
Figure 4E:
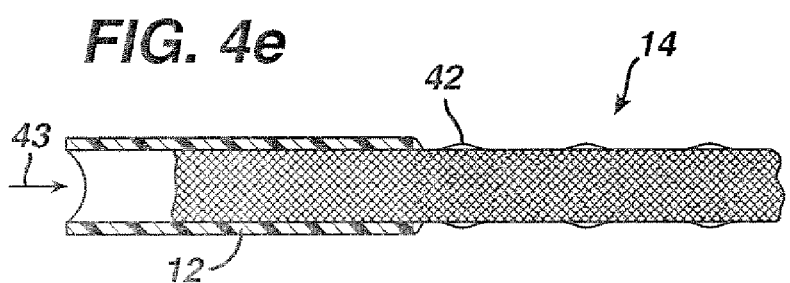

The active suture may be manufactured, for example, via steps that include: production of the fluid conducting element to be used as the internal passageway of the active suture, incorporation of the fluid conducting element into a braided suture to form the active suture, attachment of the proximal end of the fluid conducting element or active suture to a connector, and attachment of the distal end of the active suture to a suture needle. Fine tubes compatible in size and form with the active suture shown in FIGS. 1*a* and 1*b*, for example, may be produced using conventional polymer extrusion technology. The tubes may be extruded directly to the proper size or may be extruded to a larger than preferred size and subsequently reduced in size with conventional fiber drawing techniques. If coated fiber tows or coated braided sutures are selected to serve as the fluid conducting element of the active suture, as depicted in FIGS. 3*a* and 3*b*, the first step in production would involve a process for coating the braided suture or fiber tow with a continuous polymer sheath. A polymer extruder may be outfitted with a die that allows a fiber tow or braided suture to pass through and as the tow or braided suture pass through the die, they become encapsulated with a polymer film. This process is similar to the wire-coating process used to coat metal wires with insulative polymers and is well-know in the art. The tubes, coated fiber tows or coated braided sutures may be subsequently processed to form holes or channels as shown in FIGS. 4*b*, *c* and *d*. These openings in the fluid conducting element may be formed with mechanical methods or may be produced with precision laser equipment. It is important to note that in several embodiments, the step of forming a series of openings along the length of the fluid conducting element is optional. Indeed, the embodiment depicted in FIG. 4*a* simply allows the fluid to emit through the end of the truncated passageway and does not call for openings to be formed along the length of the fluid conducting element. Once the tube, coated fiber tow or coated braided suture has been formed, it may be braided along with other fiber strands to form the active suture of FIGS. 4*a*, 4*b*, 4*c* or 4*d*. This may be accomplished by passing the tube, coated fiber tow or coated braided suture along side the core filaments of a braided suture thereby allowing the woven filaments of the braided suture to encircle the tube, coated fiber tow or coated braided suture. Alternate braiding schemes wherein the tube, coated fiber tow or coated braided suture is woven around the core filaments of the braided suture may also be envisioned. After braiding, the embodiments represented in FIGS. 4*a* and 4*b* may be produced by removing a portion of the tube or coated fiber tow or coated braided suture. This may be accomplished by grasping the tube, coated fiber tow or coated braided suture with precision needle holders and pulling it through the braided suture until only a portion of the tube, coated fiber tow or coated braided suture remains inside the braided suture to form the active suture. Alternatively a polymeric tube exhibiting a smaller outside diameter than that of the braided suture may be pressed into the proximal end of the braided suture. In this way, a portion of the tube, up to several centimeters, may be positioned coaxially within the braided suture, as shown in FIG. 4a, while a portion of the same tube extends from the proximal end of the braided suture as shown in FIG. 1a. To prevent the tube from slipping out of the braided suture a small amount of adhesive may be applied at the proximal end of the braided suture to cement the tube to the multiple filaments of the braided suture. Alternate methods for attaching tubes to the proximal end of the braided suture, involving thermal bonding or the use of shrinkable polymeric sleeves, may also be envisioned.

Components of the active suture may be made from both bioabsorbable and non-absorbable materials. The sutures, tubes, coated fiber tows, coated braided sutures, adhesives, and connectors of this invention may be made from polymers that are commonly employed in the manufacture of sutures including but not limited to polypropylene, polyethylene, polyamides, polyethyleneterephthalate (PET), polytetraflouroethylene (PTFE), silk, polycaprolactone, polydioxanone, polyglycolide, polylactide, or blends of polycaprolactone, polydioxanone, polyglycolide or polylactide. Additionally, since the connectors do not necessarily become implanted in the body of the patient, they may be produced from even a broader variety of engineering polymers, including but not limited to solvent free polyvinyl chlorides, polyurethanes, polyesters, polycarbonates, polyolefins and polyamides.

Fluids that may be utilized with any of the sutures described above include any therapeutic or bioactive agent or fluid, including but not limited to antimicrobial or antibiotic agents such as 2,4,4'-trichloro-2'hydroxydiphenyl ether, benzalkonium chloride, silver sulfadiazine, povidone iodine, triclosan, gentamiacin; anti-inflammatory agents, steroidal or non-steroidal, such as celecoxib, rofecoxib, aspirin, salicylic acid, acetominophen, indomethicin, sulindac, tolmetin, ketorolac, mefanamic acid, ibuprofen, naproxen, phenylbutazone, sulfinpyrazone, apazone, piroxicam, anesthetic agents such as channel blocking agents, marcaine, lidocaine, bupivacaine, mepivacaine, procaine, chloroprocaine, ropivacaine, tetracaine, prilocalne, levobupivicaine, and combinations of local anesthetics with epinephrine, opioid analgesic agents such as morphine, fentanyl, codeine, anti-proliferatives such as rapamycin, growth factors such as PDGF, oxygen rich liquids for wound healing, scar treatment agents such as hylauronic acid, angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, loratidine, aurothioglucose, auranofin, Cortisol (hydrocortisone), cortisone, fludrocortisone, prednisone, prednisolone, 6α-methylprednisone, triamcinolone, betamethasone, and dexamethasone; hemostatic agents such as thrombin, tranexamic acid, epinephrine; as well as antithrombotic agents, biologics such as stem cells in a liquid solution, proteins, and enzymes may also be delivered through the active suture. Irrigation of the wound site may also be conducted through an active suture.

An alternate method and purpose for using the active suture would be for the extraction of fluids from the wound site. By applying a vacuum through tubing that is connected to the proximal end of the active suture, body fluids may be drawn directly from the wound site thus providing a novel means of fluid removal to compliment wound irrigation procedures. Alternatively, the fluid may be drawn from the wound and analyzed to determine the condition of the wound. For example, the chemical signature of the sampled fluid may give an indication as to the progress of wound healing, or the detection of bacteria may enable early diagnosis of an infection in the wound.

EXAMPLE 1

Figure 10A:
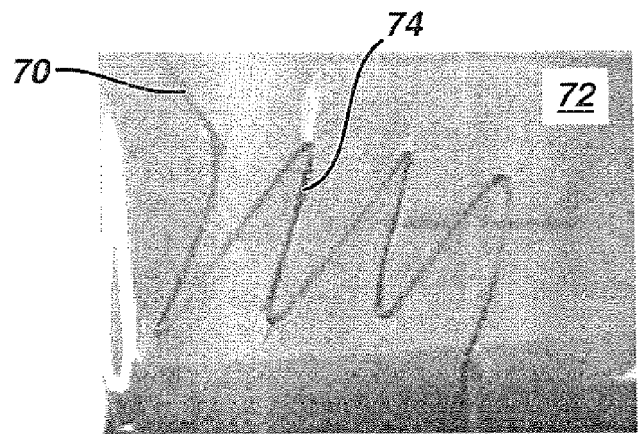
FIGS. 10a, 10b and 10c are a series of images that show the time-elapsed distribution of fluid from an active suture.
Figure 10B:
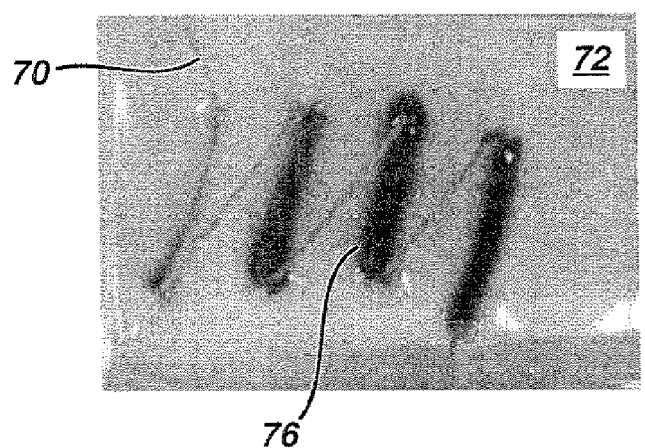
Figure 10C:
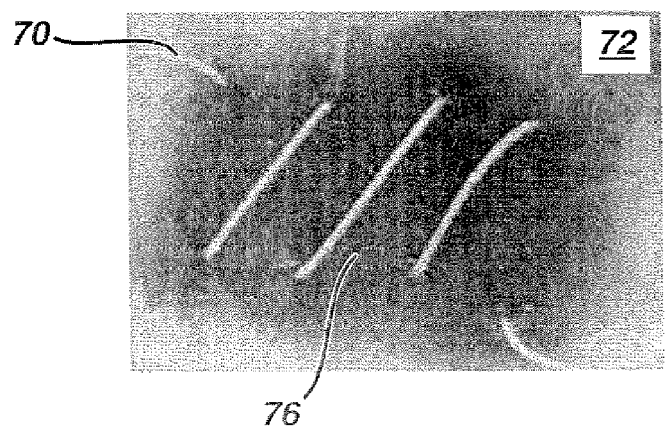

In order to demonstrate the ability of the active suture to distribute a fluid to surrounding tissue, a PET braided suture, containing a polypropylene tube that terminates within the braided suture, as depicted in FIGS. 1b, and 4a, was employed in an in vitro experiment wherein the active suture was passed multiple times though gelatin and subsequently connected to an IV delivery system that delivered water containing a blue pigment to the portion of the active suture that was imbedded in the gelatin. A series of time-elapsed images are shown in FIGS. 10a, 10b and 10c. FIG. 10a, taken at the onset of the experiment, shows the active suture 70 embedded in gelatin 72. The black mark on the active suture 74 indicates the location at which the internal passageway terminates. As time progresses, the pigment 76 spreads out around the active suture as shown in FIG. 10b. Ultimately, as shown in FIG. 10c, the fluid spreads to encompass the entire region surrounding the wound.

EXAMPLE 2

The incorporation of internal passageways into the active sutures should not compromise the tensile strength and knot tensile strength of the sutures to below standard acceptable levels if the active suture is to be used for both wound approximation and fluid infusion. The knot tensile strengths of PET braided sutures in United States Pharmacopia (USP) standard sizes of 0 and 2 that have polypropylene tubes imbedded along side their core filaments were measured according to United States Pharmacopia (USP) standard 23. Size 0 sutures contained tubes with outside diameters of approximately 130 µm and inside diameters of ~75 µm, and size 2 sutures contained tubes with outside diameters of approximately 230 µm and inside diameters of ~135 µm. For each test, at least 10 samples were tested per USP specifications. The performance of the PET braided sutures containing the polypropylene tubing at their core easily exceeded minimum performance requirements as set by USP standards, with average knot tensile strength values of 13.5 and 7.7 lbs for size 2 and 0 sutures respectively.

EXAMPLE 3

Experimental data indicates that extruded polymeric tubes produced from polypropylene, with outside diameters ranging from 0.005" to 0.010", with Youngs Moduli ranging between 0.1 and 3 GPa, with outside diameters (O.D.s) that are less than 1.7 times that of their inside diameters (I.D.s) will buckle and collapse when the braided sutures in which they are embedded are tied into square knots similar in form to those commonly used in surgical procedures. Similar experiments conducted with polymeric tubes comprised of polyethylene and polytetraflouroethylene tubes with Youngs moduli ranging between 0.1 and 3 GPa with O.D. to I.D. ratios of greater than 2.3 do not collapse completely inside the square knots of the active suture and fluid can indeed be transferred through the knotted portions. For active sutures that will be tied into knots, preferably the ratio of the O.D. to I.D. is greater than 1.7. More preferably, the ratio of the O.D. to I.D. is greater than 2.0. In these experiments, the tubes were embedded in braided sutures produced from polyethyleneterephthalate (PET) fibers with USP sizes ranging from 2-0 to 5. Other variables that influence the likelihood of collapse of the lumen inside of knots include thickness of the braided suture in which the internal passageway is imbedded, strength of the fluid conducting tube, and the overall tension applied in forming the knots.

What is claimed:

1. An active suture/needle assembly for delivering a fluid supplied under pressure, comprising
    an active suture comprising
        a braided suture having proximal and distal ends and an outer diameter, said braided suture having a plurality of interstices along at least a portion of its length; and
        a tube having proximal and distal ends and internally coaxial with at least a portion of the braided suture, said tube having one or more openings therein along at least a portion of its length, said tube having an internal passageway ranging from about 75 µm to 135 µm in diameter for conducting the fluid supplied under pressure via the one or more openings to the plurality of interstices of said braided suture;
    a surgical needle attached to the distal end of the braided suture; and
    a connector attached to the proximal end of the tube.

2. An active suture/needle/fluid source assembly for delivering a fluid, said active suture/needle/fluid source assembly comprising
    an active suture comprising
        a braided suture having proximal and distal ends and an outer diameter, said braided suture having a plurality of interstices along at least a portion of its length; and
        a tube having proximal and distal ends and internally coaxial with at least a portion of the braided suture, said tube having an internal passageway and one or more openings along at least a portion of its length for conducting the fluid to the plurality of interstices of said braided suture;
    a surgical needle attached to the distal end of the braided suture;
    a connector attached to the proximal end of the tube; and
    an external fluid source for supplying fluid under pressure, said external fluid source in fluid communication with said connector, wherein the fluid is supplied to said assembly at a pressure exceeding that which can evolve within said assembly due to capillary or diffusional phenomena.

3. The assembly of claim 2, wherein said distal end of said tube includes an opening and said distal end of said tube is disposed between said proximal and distal ends of said braided suture.

4. The assembly of claim 3, wherein said tube includes a plurality of openings.

* * * * *